(12) United States Patent
Lai et al.

(10) Patent No.: US 11,872,411 B2
(45) Date of Patent: Jan. 16, 2024

(54) METHOD OF BEAM ANGLE OPTIMIZATION FOR RADIATION APPARATUS

(71) Applicant: Yu-Jen Wang, New Taipei (TW)

(72) Inventors: Feipei Lai, Taipei (TW); Jason Chia-Hsien Cheng, Taipei (TW); Yu-Jen Wang, New Taipei (TW); Wei-Jen Chen, Taoyuan (TW)

(73) Assignee: Yu-Jen Wang, New Taipei (TW)

( * ) Notice: Subject to any disclaimer, the term of this patent is extended or adjusted under 35 U.S.C. 154(b) by 156 days.

(21) Appl. No.: 17/681,190

(22) Filed: Feb. 25, 2022

(65) Prior Publication Data

US 2023/0271032 A1    Aug. 31, 2023

(51) Int. Cl.
*A61N 5/10*       (2006.01)
*G16H 30/20*   (2018.01)
*G16H 30/40*   (2018.01)

(52) U.S. Cl.
CPC ......... *A61N 5/1067* (2013.01); *A61N 5/1031* (2013.01); *G16H 30/20* (2018.01); *G16H 30/40* (2018.01)

(58) Field of Classification Search
None
See application file for complete search history.

(56) References Cited

U.S. PATENT DOCUMENTS

| 7,266,176 | B2* | 9/2007 | Allison | A61N 5/1031 378/65 |
| 2017/0354832 | A1* | 12/2017 | Bush | A61N 5/103 |
| 2018/0021594 | A1* | 1/2018 | Papp | A61N 5/103 600/1 |
| 2019/0329073 | A1* | 10/2019 | Meltsner | A61N 5/1077 |
| 2020/0101325 | A1* | 4/2020 | Ollila | A61N 5/1039 |

* cited by examiner

*Primary Examiner* — Hoon K Song
(74) *Attorney, Agent, or Firm* — Muncy, Geissler, Olds & Lowe, P.C.

(57) ABSTRACT

A newly developed algorithm and software can effectively and accurately predict the collisions for the accelerator, phantom, and patient setups, and can help physicians to choose the noncolliding and optimized beam sets efficiently via offering the ideal hits of planning target volume (PTV) and constraints of organ at risks (OARs).

7 Claims, 2 Drawing Sheets

METHOD OF BEAM ANGLE OPTIMIZATION FOR RADIATION APPARATUS

CROSS-REFERENCE TO RELATED APPLICATIONS

Not applicable.

BACKGROUND OF THE INVENTION

Field of the Invention

The present disclosure relates to a method of beam angle optimization for radiation apparatus, and more particularly, relates to a new voxel-based method to optimize the beam angle sets during external beam radiation use.

Descriptions of the Related Art

The incidence rate of cancer in humans has increased significantly along with human life expectancy, which has become a major medical issue faced by humankind in the twenty-first century. In total, there will be approximately 1,898,160 cancer cases diagnosed, the equivalent of 5200 new cases each day estimated in 2021 in USA. In light of such, the treatment for cancer has advanced rapidly in the last few decades, resulting in treatment methods such as surgical resection or excision, radiation therapy (or radiotherapy for short), chemical therapy (or chemotherapy for short), targeted therapy, and immunotherapy, etc.

Radiotherapy (RT) cures a cancer by means of focused high-energy radiation (e.g., X-rays, electron beams, protons, or heavy particles) that destroys the genetic material, or more specifically DNA, of cancer/tumor cells to inhibit regeneration and kill those cells, and thereby reduce the tumor.

Nowadays, a lot of radiotherapies are available for use, including stereotactic ablative radiotherapy (SABR), three-dimensional conformal radiotherapy (3DCRT), intensity-modulated radiation therapy (IMRT), and volumetric-modulated arc radiotherapy (VMAT), among others. A physician would choose an appropriate treatment method based on the type of the cancer to be treated, the size and severity of the tumor, and the patient's physical conditions. SABR, for example, is an ablative radiation therapy whose precision depends on a high-standard positioning technique. SABR requires high-end radiation technology and equipment, and uses a computer to compute an optimal radiotherapy plan. As SABR allows high-dose radiation per treatment, the required number (fraction) of treatments is relatively small.

Beam angle optimization is a critical issue and is a challenging task for modern RT. Until now, it still lacks a convenient strategy to select beams wisely. Noncoplanar RT techniques may have dosimetric advantages but increase mechanical collision risk, especially for large body sizes, large immobilization equipment or with physiological monitor during RT. The present invention proposes a novel solution to offer noncolliding optimized beam angle sets for the dosimetric plan.

SUMMARY OF THE INVENTION

In one aspect, the present invention is directed to a novel solution to offer noncolliding optimized beam angle sets for the dosimetric plan during external beam radiation therapy (EBRT).

The method includes an algorithm to convert DICOM files to small voxels and to calculate the best beam angle set for EBRT. First, the DICOM files are converted into coordinate locations of Euclidean space. Then, the images of the patient would be cut into polygons for which information be recorded in the DICOM files. Then each polygon is separated into cubes since this system focuses on the relationships between the volumes been exposed of region of the interests (ROIs) and planning target volume (PTV). Set the Isocenter as (0, 0, 0) and other devices of the accelerator such as the couch (Xc, Yc, Zc), the plate (Xp, Yp, Zp), and the gantry (Xg, Yg, Zg) at the relative location with respect to the isocenter. The couch and the plate are allowed to rotate by the z axis defined as <k> or <0, 0, 1> with the rotation matrix. The gantry and its components are allowed to rotate by the x axis defined as <i> or <1, 0, 0> with the rotation matrix. The cubes of patient would be placed on the plate so the same rotation of the plate could be applied.

Since the hit frequencies are used to value the quality of the beam sets, this system will ask the users to enter their goal of their ideal hit frequencies. The radiation dose used clinically would be thought as the quantity of collision hit frequencies. A set of beam angles would be provided after the above computing process. The information of each beam angle would be entirely collected as a set B with connections of the entered hit frequencies.

Each component in the above set $B_{[41]}$ could be separated into set b which states for the secondary beam block field and the number of b decided by the thickness of the leaf on the gantry gun and the region of the PTV projected to the section with respect to the beam angle. The optimization of picking arcs is computed by the adjustment of those secondary component b, also known as the adjustment of the leaves.

The system is now allowed to identify any arc which could be generated after the collection of beam angle information. All the arcs and its transforms are put into a set A for the further comparisons. The transforms are arcs with different beam block field adjustments which have a variety of advantages over different ROIs. Rankings according to different ROIs would be conducted with the components in the above set A. The system would select a set of arcs which has the advantage over the collision between the radiation and the ROI cubes. The result could be shown at the output file or a briefly constructed system of hit diagram (states for the heat diagram in traditional dose).

DESCRIPTION OF THE PREFERRED EMBODIMENT

The present disclosure will become more fully understood from the following detailed description and accompanying drawings.

Figure 1:
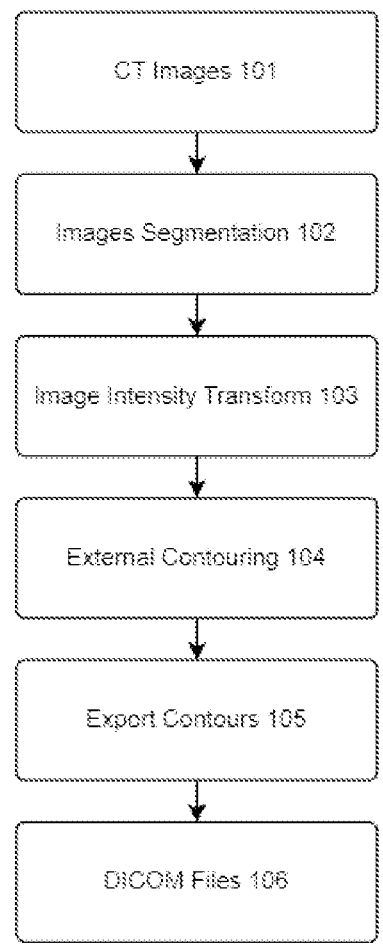
FIG. 1 is a process of automatic computed tomography (CT) contouring and image exporting.

Please refer to FIG. 1, it illustrates a process of automatic computed tomography (CT) contouring and image exporting. The simulation CT images were subject to image segmentation, image intensity transformation, and region of interest (ROI) processing, and the contours were exported as Digital Imaging and Communications in Medicine (DICOM) files. For comprehensive collision prediction, the contoured subjects included the body surface, auxiliary equipment such as a shell or a vacuum bag, and other accessories above the CT couch plate. A user interface (UI) was designed to help users choose their own intensity transformation specifications. The grayscale morphological closing technique from the field of computer vision was applied to smooth the images. The functions of dilation, erosion, and contour finding for grayscale images were implemented using the Open Source Computer Vision (OpenCV) library. The isocenters of the CT images were defined manually. Finally, the DICOM images were exported and saved in the secured space. The process can be illustrated in FIG. 1, Step 101, Step 102, Step 103, Step 104, Step 105 and Step 106.

Figure 2:
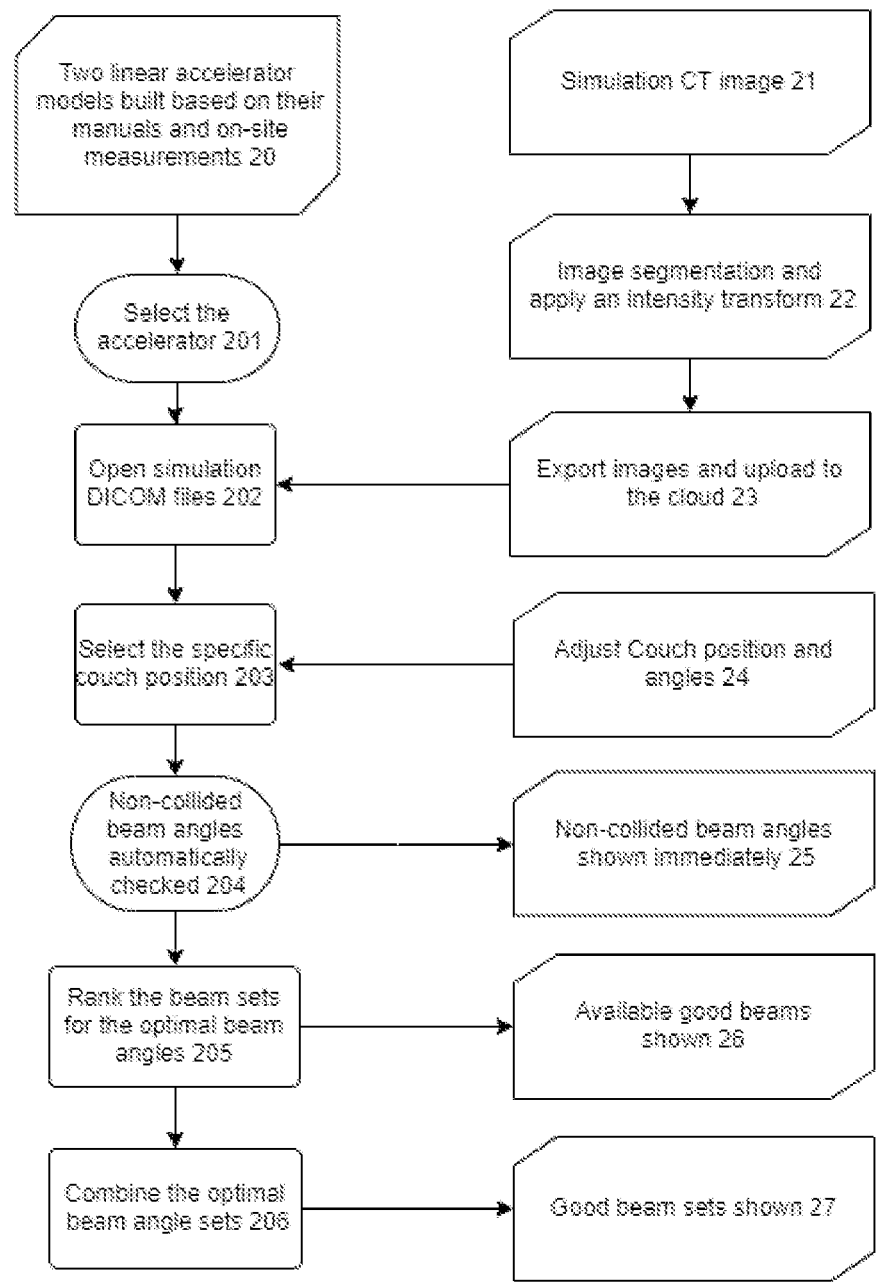
FIG. 2 is a flow chart of the method disclosed in the present invention.

Please refer to FIG. 2, it illustrates the process of bean angle optimization of the present invention.

The process of beam angle optimization could be summarized as follows:

Step 201: Select the accelerator.
Step 202: Open simulation DICOM files.
Step 203: Select the specific couch position
Step 204: Non-collided beam angles automatically checked.
Step 205: Rank the beam sets for the optimal beam angles
Step 206: Combine the optimal beam angle sets.

In Step 201, two linear accelerator models were previously built based on their manuals and on-site measurements (Step 20).

In Step 202, there are some preparations. CT image is stimulated in Step 21. The Step 22 of Image Segmentation and apply an intensity transformed follows the Step 21. In Step 22, the images of the tumors and organs are segmented into voxels. After Step 22, the images are exported and uploaded to the cloud (Step 23). After above preparations, Step 21, Step 22 and Step 23, the simulation DICOM files can be opened (Step 202).

The CT images are read as sets of vectors drawn by the user. In order to generate the meshes, polygons, and cubes, the vectors are aligned by the isocenter which is positioned by the user. The meshes, polygons, and cubes are later created by layers of vectors.

In Step 203, the specific couch position is selected by referencing the DICOMS files opened in Step 202 and adjusting couch position and angles (Step 24). In Step 24, the patient is aligned to the right position.

After the examination of device collision detection, the allowable beam angles sets are ensured. We then simulate the overlap between the beams from the gantry gun and both the PTV and OARs according to the mentioned allowable beam angles. All the simulation conditions and results of hit frequency are recorded for the further optimization.

In Step 204, non-collided beam angles are automatically checked and therefore, non-collided beam angles are shown immediately in Step 25.

With the constraints the user has suggested, a relation between the ranking score or advantage of the beams could be parameterized.

In Step 205, the beam sets for the optimal beam angles are ranked. Since all the possible beam angles are simulated, available good beams are shown in Step 26. Before Step 26, the goal of PTV and constraints of organ at risk (OARs) shall be imported.

In Step 206, the optimal beam angle sets are combined and therefore, good beam sets are shown in Step 27. Furthermore, between Step 205 and Step 206, the beam field shape is adjusted and the hit frequency of PTV and OARs is calculated.

More particularly, the present invention is a voxel-based method by recording and calculating the coordinate locations of Euclidean space to optimize the beam angle sets of external beam radiation therapy.

Virtual models for preciously simulation are built. After importing the DICOM of patient the present invention relocates all the device to align the isocenter of DICOM. The representations of each component of the device has been mentioned in the summary.

Since the organs are cut into arranged voxels, it is easy for the present invention to calculate the volume of each region of interest. Four rays are created from the beam source of gantry gun to define the region of the patient that would be hit by the radiation. The algorithm would calculate all the voxels in the region as the colliding voxel even though the voxel gets only $1/10$ inside the region, in case it's more conservative. A set RB would collect the bound formed by the ray, $\{Bi(d), I=1, 2, 3, 4\}$, d states for the distance from the cube to the virtual plane orthogonal to the beam and including the source. Based on RB, it is easy to define which voxel is triggered by the radiation or not. Then, the collided volume could be calculated precisely.

Recognizing that solving the problem without such constraints would never exist an optimal solution. Not only the constraints of oncology and the operation of device that should be considered, but also some strategies have to be decided to force the output of the optimization is practical. The calculation is executed with each voxel been weighted by the doctor and the coverage of plan target volume is considered as the view of weighted voxels. The rankings of the intersection of the minimum organ at risk and the maximum of PTV would be decided by the score computed by the summary of the weight of voxels. It is still a pie in the sky to simulate all the situations including those useless conditions such as suspending leaf or extreme field blocks. In order to assure the plan thus designed is practical, the filed blocks are controlled lightly and focused on distinguish organ at risk. As mentioned in the summary, all the situations of voxels been collided in each beam angle are record in a set A $\{B\_cg, \forall c \in C, g \in G\}$, B states for the beam could be used, C is the set of couch angle allowed to rotate, and G is the set with respect to each C. The substructure b of B is the divided unit that could adjust the collision situation or, in other words, the beam field block controlling. According to the constraints that have been set previously and the score of weighted voxels, the demanding voxel-based coverage of the planning target volume while executing any beam block field adjustment is maintained. It seems like the problem has been solved, but there is still a catastrophic issue, "favoritism". The result would be strongly decided by the constraints of organ at risk. After lots of trials, it can be found that it's better to achieve the general goal of dose (same as hit per voxel in our point of view) by a gradual-equalitied way. Instead of picking the arcs with the best score, the present invention makes individual rankings for different organs at risk of arcs and further generates the new arc set from picking the best arc in each ranking until the performance of the result drops. It balances the harm of each organ at risk. The present invention can be used to adjust the result to achieve some other demand if needed.

Below is an embodiment by operating a software using the method of the present invention:

1. Adjust the couch plate

Adjust the couch plate to fit the lying computed tomography model, the collision of the accelerator could also be checked at the same time 2. Import DICOM Switch the user interface (UI) to "Open DICOM"

The DICOM could be imported by the local address or from the cloud.

The layers of DICOM would be cut into cubes after the importing process.

3. Set constraints of planning target volume (PTV) that are needed

Switch the UI to "Optimization"

Choose the treated target from region of interest (ROI) of the upper dropdown list as PTV.

Choose "PTV" at the lower dropdown list.

Fill in the goal of hit (collided frequencies) at the third input field.

Press "Set Constraint" and make sure that the system informs.

4. Constraints of organs at risk (OARs) that are needed

Choose the avoiding target ROI of the upper dropdown list as an OAR.

Choose the type of OAR at the lower dropdown list.

Set the constraints of each OAR

Set the goal of hit (collided frequencies) at the third input field.

Press "Set Constraint" and make sure that the system informs.

5. Press "Check Beam Angles" to run through all the usable noncolliding beams. It collects the information and computes some results for the beams.

6. Press "Offer Optimized Arcs" to calculate the arcs that could be used.

The arcs would be created by continuous beam angles that could be modified for the purpose of OAR-avoidance and with the area changed less than the demand of the accelerator.

7. Pressed "Start Optimization" to get a set of arcs based on the set constraints.

The set the software provides would be some arcs that dominate the performance based on the spatial dodging. The decision between OARs is controlled by some greedy strategies and even benefit to each OAR if there is no other demand (default).

For someone who would not like to get too many couch angles, you can set the constraints of the number of couch angles before the "Start Optimization".

8. Press "Hit Diagram" to get the diagram of hit-percent diagram.

9. Switch the UI to "Analysis" to show the hit diagram.

Although the above embodiment was illustrated by using VMAT, the software using the method of the present invention can also applied to other techniques to output beam sets such as Step and Shoot, techniques with fixed gantry and other similar techniques as well.

The various embodiments of the methods of this invention that are described above are illustrative only of the principles of this invention and are not intended to limit the scope of the invention to the particular embodiment described. Thus, the invention is limited only by the following claims.

What is claimed is:

1. A method of beam angle optimization for radiation apparatus, including the following steps in sequence:
   selecting an accelerator;
   opening a simulation DICOM file;
   selecting a specific couch position;
   checking non-collided beam angles; and
   ranking the beam sets for the optimal beam angles.

2. The method of claim 1, wherein the DICOM file is prepared from an image subject to image segmentation, image intensity transformation, and region of interest (ROI) processing.

3. The method of claim 2, wherein the specific couch position is selected by referencing the DICOMS file and adjusting a couch position and angles.

4. The method of claim 3, wherein the non-collided beam angles are checked and non-collided beam angles are shown immediately.

5. The method of claim 4, wherein the beam sets for the optimal beam angles are ranked and available good beams are shown.

6. The method of claim 5, wherein the optimal beam angle sets are combined and good beam sets are shown.

7. The method of claim 1, further comprises a step of adjusting a beam field shape and calculating a hit frequency of planning target volume (PTV) and constraints of organ at risk (OARs) between the step of checking non-collided beam angles and the step of ranking the beam sets for the optimal beam angles.

* * * * *